(12) United States Patent
Hingley et al.

(10) Patent No.: US 9,027,385 B2
(45) Date of Patent: May 12, 2015

(54) AEROSOL SENSOR

(75) Inventors: Brian Hingley, Alexandria (AU);
Michael Potas, Alexandria (AU)

(73) Assignee: Saban Ventures Pty Limited, New South Wales (AU)

( * ) Notice: Subject to any disclaimer, the term of this patent is extended or adjusted under 35 U.S.C. 154(b) by 884 days.

(21) Appl. No.: 13/002,003

(22) PCT Filed: Jun. 30, 2009

(86) PCT No.: PCT/AU2009/000841
§ 371 (c)(1),
(2), (4) Date: Mar. 25, 2011

(87) PCT Pub. No.: WO2010/000021
PCT Pub. Date: Jan. 7, 2010

(65) Prior Publication Data
US 2011/0167895 A1    Jul. 14, 2011

(30) Foreign Application Priority Data

Jun. 30, 2008  (AU) ................................ 2008903352

(51) Int. Cl.
*G01N 25/18* (2006.01)
*G01N 25/40* (2006.01)
(Continued)

(52) U.S. Cl.
CPC .. *A61L 2/26* (2013.01); *A61L 2/186* (2013.01); *A61L 2/22* (2013.01); *A61L 2/28* (2013.01); *A61L 2202/14* (2013.01); *G01K 13/02* (2013.01)

(58) Field of Classification Search
USPC ............ 436/135; 422/26, 31, 82.02; 73/25.01
See application file for complete search history.

(56) References Cited

U.S. PATENT DOCUMENTS 3,579,097 A * 5/1971 Luden ........................... 324/439
4,305,724 A * 12/1981 Micko ........................... 436/156
(Continued)

FOREIGN PATENT DOCUMENTS

JP     05-322739     12/1993
JP     05-332796     12/1993
(Continued)

OTHER PUBLICATIONS

Sano, "Gas Sensor," Patent Abstracts of Japan, JP-2005-098846, TDK Corp, Apr. 14, 2005.
(Continued)

*Primary Examiner* — Lisa Caputo
*Assistant Examiner* — Punam Roy
(74) *Attorney, Agent, or Firm* — Finnegan, Henderson, Farabow, Garrett & Dunner, LLP

(57) ABSTRACT

A method of measuring density of a sterilant aerosol e.g. aqueous hydrogen peroxide, in a gas stream (such as a stream of air) for the purposes of measuring sterilant dosage comprising: passing a gas stream at flow rate past an electrically heated element and measuring a first cooling effect, passing an aerosol suspended in a gas stream at flow rate past an electrically heated element and measuring a second cooling effect and measuring the difference between the first cooling effect and second cooling effect and correlating the difference with aerosol density. The total dosage can thus be determined. A measured dosage of a sterilant aerosol can be delivered by way of a feedback loop to halt further delivery of sterilant aerosol when the amount of aerosol delivered reaches a predetermined dosage. The methods allow sterilization to be certified.

25 Claims, 3 Drawing Sheets

Figure 1:
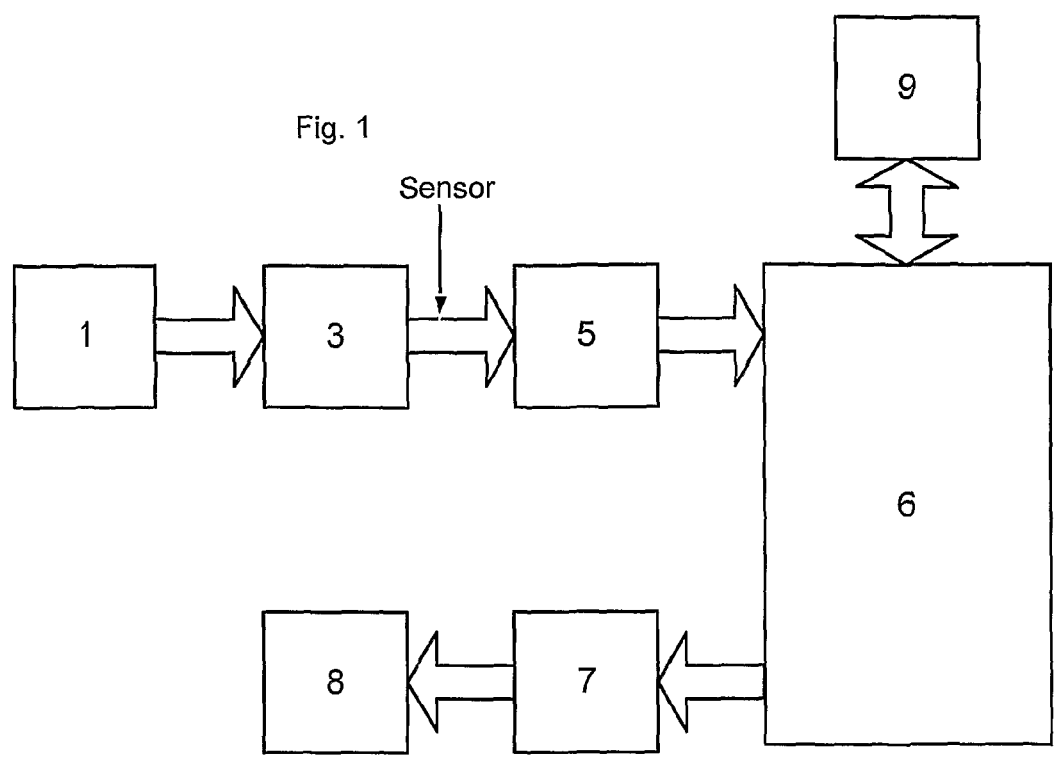

(51) Int. Cl.
*A61L 2/26* (2006.01)
*A61L 2/22* (2006.01)
*A61L 2/28* (2006.01)
*G01K 13/02* (2006.01)
*A61L 2/18* (2006.01)

(56) References Cited

U.S. PATENT DOCUMENTS

| | | | | |
|---|---|---|---|---|
| 4,512,951 | A * | 4/1985 | Koubek | 422/33 |
| 5,371,469 | A * | 12/1994 | Anderson | 324/705 |
| 5,600,142 | A * | 2/1997 | Van Den Berg et al. | 250/339.13 |
| 5,789,258 | A * | 8/1998 | Drinkwine et al. | 436/174 |
| 5,847,392 | A * | 12/1998 | Van Den Berg et al. | 250/339.09 |
| 5,847,393 | A * | 12/1998 | Van Den Berg et al. | 250/339.13 |
| 5,989,398 | A * | 11/1999 | Young et al. | 204/424 |
| 6,071,476 | A * | 6/2000 | Young et al. | 422/51 |
| 6,318,151 | B1 | 11/2001 | Wang et al. | |
| 6,627,150 | B1 * | 9/2003 | Wang et al. | 422/33 |
| 6,656,426 | B1 * | 12/2003 | Wang et al. | 422/27 |
| 8,178,357 | B2 * | 5/2012 | Trogler et al. | 436/135 |
| 8,591,808 | B2 | 11/2013 | Berentsveig et al. | |
| 2003/0039299 | A1 | 2/2003 | Horovitz et al. | |
| 2003/0124026 | A1 * | 7/2003 | Williams et al. | 422/33 |
| 2003/0235925 | A1 * | 12/2003 | Bonne et al. | 436/181 |
| 2006/0188994 | A1 * | 8/2006 | Ding et al. | 436/3 |
| 2007/0180933 | A1 * | 8/2007 | Grate et al. | 73/863.12 |
| 2008/0233001 | A1 * | 9/2008 | Ricciardi et al. | 422/20 |
| 2009/0007636 | A1 * | 1/2009 | Starling | 73/31.02 |
| 2009/0084201 | A1 * | 4/2009 | Almirall et al. | 73/864.81 |
| 2014/0339323 | A1 * | 11/2014 | Bentvelsen et al. | 239/11 |

FOREIGN PATENT DOCUMENTS

| | | |
|---|---|---|
| JP | 06-331641 | 12/1994 |
| JP | 2009-502489 | 1/2009 |

OTHER PUBLICATIONS

International Search Report from the Australian Patent Office for International Application No. PCT/AU2009/000841 (Mail date Jul. 23, 2009).

* cited by examiner

AEROSOL SENSOR

CROSS REFERENCE TO RELATED APPLICATION

This application is a national phase application based on PCT/AU2009/000841, filed Jun. 30, 2009, which claims the priority of Australian Patent Application No. 2008903352, filed Jun. 30, 2008, the content of both of which is incorporated herein by reference.

TECHNICAL FIELD

This invention relates to a method and apparatus for determining the density of an aerosol in a gas stream, and the use thereof for quantifying the amount of aerosol delivered to a sterilizing chamber.

BACKGROUND ART

Any discussion of the prior art throughout the specification should in no way be considered as an admission that such prior art is widely known or forms part of common general knowledge in the field.

Sterilizers are used in medical, food and packaging industries to prevent the transmission of agents such as spores, fungi and bacteria. A typical sterilizer creates a set of physical conditions in a sterilization chamber that can effectively kill nearly all of these transmissible agents.

One way of determining whether there has been sufficient exposure to the sterilant is to place test strips bearing a known micro-organism load in the sterilization chamber and to count the number of surviving micro organisms at the end of the sterilization process. That is time consuming, labour intensive, and impractical.

Alternatively, parametric monitoring can be employed in which measurements or controls are used to ensure that proper sterilization conditions are attained. Regulatory requirements for medical devices dictate that sterilizers have systems to verify the completion of a successful sterilization cycle. Time and temperature are two key parameters that need to be monitored for thermal sterilizers (autoclaves), and both of these are easily monitored with current technologies. In the case of sterilisers that use liquid chemical sterilants, regulatory requirements specify that the concentration or dosage of the sterilization chemistry delivered to the sterilization chamber must also be monitored. Once all the values for the necessary parameters are met, then it is possible to certify the articles as sterile and release them for use.

However, due to the corrosiveness of typical disinfection agents, measuring the dosage or concentration delivered is not a trivial matter, making certification of sterilisation difficult.

Sterilization processes which use an aerosol of microdroplets of a liquid sterilant in a gas stream (usually air) are known to be highly efficacious. These processes use, for example, an aerosol of droplets of hydrogen peroxide solution dispersed in an air stream which are kept in contact with an article to be sterilized for a predetermined time. These pose problems not only with the corrosive nature of the materials, but also the fact that a heterogeneous mixture (droplets in a gas) needs to be measured.

As used herein, the term "concentration" is used to refer to the amount or volume of active sterilising agent (such as hydrogen peroxide) relative to the amount or volume of inert carrier fluid (usually water) present. The term can be used in relation to a bulk liquid, to an individual aerosol particle, or to a collective group of aerosol particles generally, although it is not necessary that all particles in an aerosol have the same concentration, for example, if an aerosol arises from two different sources or if an aerosol has been partially modified in space or time.

The term "density" in relation to an aerosol refers to the amount of the total volume that is filled with aerosol particles. The density is a measure of a combination of aerosol droplet volume and the number of aerosol droplets per unit volume. Larger droplets or a higher number of droplets per unit area will both increase aerosol density, whereas smaller droplets or fewer droplets per unit volume will both decrease aerosol density.

The dosage of sterilant delivered is a function of the concentration, the density and the delivery time.

In order to verify sterilization, the dosage (i.e. the density delivered multiplied by the delivery time) of the liquid sterilant delivered to the sterilization chamber must be measured. If the article is exposed to too small a dose of sterilant, then sterilization cannot be certified and parametric release cannot take place. However, simply using a large excess of sterilant is not a practical option, since if the article is exposed to too high a dose, condensation of the aerosol droplets can take place on the surface of the article, leading to occlusion of the surface with used sterilant, which can result in reduced efficacy. Further, condensation can lead to the presence of residual sterilant on the apparatus to be sterilized. This can pose unacceptable risks to staff and patients, and the time needed to wash or dry the article may be longer than would otherwise be necessary, resulting in an unnecessarily long cycle time.

The present applicants have reasoned that if the concentration of sterilant in the solution being nebulised is known, then if the density of the aerosol droplets in the gas can be precisely determined (a quantified value of the mass of aerosol droplets in a given volume of the gas stream. e.g. grams of aerosol per $m^3$ of gas) then the dose supplied to an article to be sterilized in a given time can be monitored. It would then be possible to use parametric monitoring to certify an article as sterile.

Hitherto there has been no simple, reliable and reproducible means for determining the density of an aerosol in a gas stream which was suitable to provide parametric monitoring data.

In the past aerosol density has been measured by optical means in which a gas flow containing an aerosol passes between a light source and a photo detector located on opposite sides of the gas flow path. A reduction in light detected by the photo detector is correlated with aerosol density by calibration and then used to indicate density. Initially unpublished attempts were made to measure changes in density optically and to combine those measurements with flow measurements. However the results were not acceptable for a variety of reasons.

Optical methods for estimating aerosol density suffer from a number of disadvantages. Generally, both light source brightness and photo detector sensitivity vary over time so that frequent recalibration of apparatus is required. Condensation on either the light source or detector lenses is a problem which requires the use of wipers or gas jets directed to prevent or remove condensates from the lens surface—a solution which introduces mechanical complexity and disturbs flow dynamics in the sterilization apparatus. Furthermore, reflection and diffraction of light by particles may cause light scattering rather than merely obscuration of part of the beam and result in measurements being influenced non linearly by variations in particle size or concentration.

In addition simple and economical optical methods are unable to measure the flow rate of the gas carrier. This would require some other flow rate measurement means and it would be advantageous if the aerosol density and gas stream flow rate could be measured with one transducer.

Alternative approaches avoiding direct aerosol measurement altogether involve the measurement of the sterilant liquid level in the nebuliser. By measuring the liquid level in the nebuliser before nebulisation, then measuring the liquid level after nebulisation, it is possible to calculate the total dosage of sterilant that has been nebulised. However, in practical terms, the amount of sterilant used is generally very small, meaning that a liquid level sensors need to be very accurate and repeatable to measure dosage. Devising a sensor to operate within the environment of a nebuliser that can accurately measure dosage levels is extremely difficult to achieve in practice.

There is a need for an improved method and apparatus for reliably determining the flow rate of a nebulant entrained in a gas stream over a range of flow rates and which is suitable for parametric monitoring. The invention is herein described primarily with reference to sterilization by means of a nebulant but the invention is not limited to use in sterilization, and those skilled in the art will appreciate that this method is suitable for any system where aerosol density and/or flow are desired to be known.

It is an object of the present invention to overcome or ameliorate at least one of the disadvantages of the prior art, or to provide a useful alternative.

SUMMARY

According to a first aspect the invention provides a method of measuring the density of a sterilant aerosol in a gas stream for the purposes of measuring sterilant dosage comprising passing an aerosol suspended in a gas stream at flow rate past an electrically heated element and measuring a cooling effect According to a second aspect the invention provides a method of measuring density of a sterilant aerosol in a gas stream for the purposes of measuring sterilant dosage comprising:
 i) passing a gas stream at flow rate past an electrically heated element and measuring a first cooling effect:
 ii) passing an aerosol suspended in a gas stream at flow rate past an electrically heated element and measuring a second cooling effect;
 iii) measuring the difference between the first cooling effect and second cooling effect and correlating said difference with aerosol density.

If the flow rate is unknown, it is maintained at a constant rate when the first and second cooling effects are measured.

The quantity of aerosol suspended in a gas stream may be known or unknown.

According to a third aspect the invention provides a method of measuring a dosage of a sterilant aerosol delivered to a chamber comprising:
1) measuring density of a sterilant aerosol in a gas stream by:
 i) passing a gas stream at flow rate past an electrically heated element and measuring a first cooling effect:
 ii) passing an aerosol suspended in a gas stream at flow rate for an aerosol delivery time past an electrically heated element and measuring a second cooling effect;
 iii) measuring the difference between the first cooling effect and second cooling effect and correlating said difference with aerosol density; and
2) using flow rate, aerosol delivery time and aerosol density to calculating the amount of aerosol delivered.

According to a fourth aspect the invention provides a method of providing a measured dosage of a sterilant aerosol delivered to a chamber comprising:
1) measuring density of a sterilant aerosol in a gas stream by:
 i) passing a gas stream at flow rate past an electrically heated element and measuring a first cooling effect:
 ii) passing an aerosol suspended in a gas stream at flow rate for an aerosol delivery time past an electrically heated element and measuring a second cooling effect;
 iii) measuring the difference between the first cooling effect and second cooling effect and correlating said difference with aerosol density;
2) using aerosol delivery time and aerosol density to calculating the amount of aerosol delivered; and
3) halting further delivery of sterilant aerosol when an amount of aerosol delivered reaches a predetermined dosage.

According to a fourth aspect the invention provides a method of sterilizing for the purpose of certifying as sterile, an article by contacting said article with a sterilant aerosol, and wherein the dosage of sterilant aerosol is measured by:
1) measuring the density of a sterilant aerosol in a gas stream by:
 i) passing a gas stream at flow rate past an electrically heated element and measuring a first cooling effect:
 ii) passing an aerosol suspended in a gas stream at flow rate for an aerosol delivery time past an electrically heated element and measuring a second cooling effect;
 iii) measuring the difference between the first cooling effect and second cooling effect and correlating said difference with aerosol density; and
2) using flow rate, aerosol delivery time and aerosol density to calculate the amount of aerosol delivered.

The certification method of the present invention further includes the step of comparing the delivered dosage of aerosol with a predetermined certification dosage, and certifying the article as sterile if the delivered dosage is at or greater than a predetermined certification dosage, or not certifying the article as sterile if the delivered dosage of aerosol is less than the range of the predetermined certification dosage.

Alternatively, the certification method of the present invention further includes the step of comparing the delivered dosage of aerosol with a predetermined certification dosage range, and certifying the article as sterile if the delivered dosage is within the range of a predetermined certification dosage, or not certifying the article as sterile if the delivered dosage of aerosol is outside of the range of the predetermined certification dosage.

In the above aspects, the first cooling effect is preferably measured with no suspended aerosol present. Although the present application is described with reference to a first cooling effect and a second cooling effect, these effects can be measured in any order, i.e. the second cooling effect described can be measured before the first cooling effect is measured if desired.

Preferably, the sterilant aerosol is an aqueous solution of hydrogen peroxide. The sterilizing agent may be advantageously a 35% hydrogen peroxide solution, nebulised by for example by means of an ultrasonic transducer. However, other sterilizing agents may be used, and they may be nebulised by any other known means. The sterilant aerosol may also include droplets which are not individually sterilant, for example, the sterilant aerosol may be made up of two or more component aerosols, only one of which is active. An example of such a component mist would be a mist made up of nebulised peroxide, combined with separately nebulised water.

Preferably the gas stream has a known flow rate. Preferably the gas is air, driven by a fan, compressor or the like. However the gas need not be air and the flow rate need not be known.

Preferably the heated element temperature is greater than or equal to the vaporisation point of said aerosol Preferably the heated element is coupled to a temperature sensitive element that measures the temperature of said heated element The cooling effect may be measured by using said temperature sensitive element in a feedback loop control system to electrically maintain said heated element to a preset temperature, wherein said cooling effect is measured by the heating effort required or part thereof to maintain said preset temperature Alternatively the cooling effect is measured by using said temperature sensitive element to measure temperature of said heated element, wherein said cooling effect is measured by measuring the temperature of said heated element.

In some embodiments, the heated element and the temperature sensitive element are one and the same.

The heated element and or temperature sensitive element may independently be an RTD or a transistor.

Preferably the aerosol density is measured by a circuit that comprises at least a resistive heater maintained at a steady state temperature. More preferably the resistive heater is a Resistance Temperature Detector ("RTD"), and most preferably a flat film type RTD, although wire wound types may also be used.

The method of the present invention may also further include the step of measuring the gas stream flow rate by comparing the cooling effect on the sensor of the gas flow with predetermined values for the cooling effect of gas flow rate. Preferably the predetermined values for the cooling effect of gas flow rate are determined at given temperatures and humidities.

In another aspect the invention provides a method of maintaining a constant flow of an aerosol comprising:
1) measuring density of an aerosol in a gas stream by:
  i) passing a gas stream at flow rate past an electrically heated element and measuring a first cooling effect:
  ii) passing an aerosol suspended in a gas stream at flow rate for an aerosol delivery time past an electrically heated element and measuring a second cooling effect;
  iii) measuring the difference between the first cooling effect and second cooling effect and correlating said difference with aerosol density;
2) maintaining the second constant cooling effect at a constant or predetermined value by controlling gas stream flow rate.

In another aspect the invention provides a method of providing a known dosage of an aerosol comprising:
1) measuring density of an aerosol in a gas stream by:
  i) passing a gas stream at flow rate past an electrically heated element and measuring a first cooling effect:
  ii) passing an aerosol suspended in a gas stream at flow rate for an aerosol delivery time past an electrically heated element and measuring a second cooling effect;
  iii) measuring the difference between the first cooling effect and second cooling effect and correlating said difference with aerosol density;
2) maintaining the second constant cooling effect for a predetermined time at a predetermined value.

Preferably the second cooling effect is maintained at a constant value by controlling nebuliser output. Preferably, nebuliser output is controlled by varying nebuliser transducer drive voltage.

Alternatively, the second cooling effect is maintained at a constant value by varying gas stream flow rate. Preferably, the gas stream flow rate is controlled by varying fan speed or voltage.

DESCRIPTION OF THE INVENTION

A schematic diagram of apparatus suitable for use in the present invention is shown in FIG. 1, however, it is conceivable that those in the art could use other aerosol sterilisation apparatus in accordance with the method described herein without deviating from the spirit of the present invention.

An article to be sterilised, such as an endoscope or the like, is placed by the operator into the sterilisation chamber 6. The chamber is then closed. During the sterilant delivery phase, the inlet valve 5 is opened and outlet valve 7 is closed. The fan 1 is engaged, generating a gas stream into the nebuliser 3. The nebuliser is, for preference, an ultrasonic nebuliser. A number of commercially available ultrasonic nebulisers are available which may be used in the present invention. The nebuliser 3 contains the liquid sterilisation agent, 35% hydrogen peroxide and is activated with the fan or shortly after the fan is turned on. The nebuliser generates droplets that are carried by the gas stream to create an aerosol which travels into the sterilisation chamber. The sterilant concentration in the aerosol stream can be adjusted by changing either the flow rate of the gas stream, the productivity of the nebuliser, or the concentration of the initial liquid sterilant that is nebulised. The passive waste removal vent or system 9 allows some gas flow to pass through it, equalising pressure and allowing the sterilisation chamber to remain at approximately room pressure. This passive system may typically include a pathway for flow to the outside air past catalytic elements that react with any sterilant and break the sterilant down into a safer chemistry suitable for disposal.

During the sterilant delivery phase, the aerosol droplets contact the surface of the article to be sterilised, as well as the inner surface of the chamber. The small size of the droplets, especially relative to their surface area, enables them to spread in a uniformly thin manner over the surface of the article, as well as access small areas, in some cases even mated surfaces.

At the end of the delivery phase, the fan 1 and the nebuliser 3 are deactivated and the air inlet valve 5 is closed. The exit valve 7 is opened and aerosol is removed with the active sterilant removal/waste system 8, which may include a pump that pulls aerosol and vapour out of the sterilisation chamber at a high rate. The gas flow removes unused aerosol from the chamber, and also removes aerosol from the surface of the article to be sterilised, and from the chamber walls. With the nebuliser off, the fan 1 may also be used to assist in the aerosol removal phase. This has the advantage of removing any unused and/or condensed aerosol from the aerosol delivery pathway. If the aerosol delivery pathway is kept dry and free from any material, such as residual peroxide, the measuring of subsequent doses of aerosol can be made with more confidence.

The removal system may include a pathway for flow between the sterilisation chamber and outside air past catalytic elements that react with the sterilant and break the sterilant down into a safer chemistry suitable for disposal. Passive vent 9 allows a source of fresh air to be drawn into the sterilisation chamber from the outside air.

The switching of the various components of the apparatus is generally under software control, to ensure appropriate operation of the fan, nebuliser and valves in correct order, and to ensure that the timing is accurately controlled. The device may also incorporate flow sensors in line between the nebuliser and sterilising chamber and/or liquid level sensors in the nebuliser to measure when predetermined levels of sterilant have been administered to the chamber or used by the nebuliser. Additionally, the surface of the sterilisation chamber may be electronically heated to a controlled temperature by thermostat means or otherwise, hence accelerating the speed of sterilisation (as is well known to those skilled in the art).

In one embodiment of the present invention as shown in FIG. 1, an aerosol sensor is placed in fluid communication between the nebuliser 3 and the inlet valve 5 to the sterilisation chamber. In the first step of this embodiment, the fan is activated, valve 5 is opened and the nebuliser is remains deactivated. This causes a gas flow to pass by the sensor and into the chamber. The sensor, the operation of which is described below in more detail, gives a first reading which is influenced by the humidity, temperature and flow rate of the gas. Based on the value of this first reading, the software then selects a precalculated dosage calibration curve.

The nebuliser 3 is then switched on, which generates the sterilant aerosol particles. These particles enter the airflow and then flow past the sensor and into the sterilisation chamber. The sensor is then read again to give a second reading which is influenced by the aerosol concentration, humidity, temperature and flow rate. This second reading is then input into the precalculated dosage calibration curve selected previously.

The difference in readings reflects the aerosol density, ie how many grams of liquid are present per unit volume of aerosol. The flow rate is generally known—either form the characteristics of the machine, or derived from the first measurement, where humidity and temperature are measured independently. The time is also measured. So, using the following relationship:

Mass of sterilant (g)=rate of deposition on heated sensor (g/s)×flow time (s), the mass of sterilant delivered can be determined. The rate of deposition is related to both aerosol density and flow rate. This mass value can be further elaborated to calculate the amount of an active sterilant delivered in systems where a sterilant in a solvent (ie $H_2O_2$ in water) is used.

The deposition rate increases with both flow and aerosol density. For a given flow rate, the deposition rate is thus directly related to aerosol density (and vice versa, for a given aerosol density, the deposition rate is directly related to the flow rate). In the present specification, unless the context indicates to the contrary, references to "aerosol density" are intended to encompass the more rigorous definition of the "rate of deposition of droplets on the heated element".

The precalculated dosage calibration curve may be devised by performing experiments where known and varying aerosol densities are placed in the presence of other controlled conditions such as varying air temperatures, humidities and flow rates.

Figure 2:
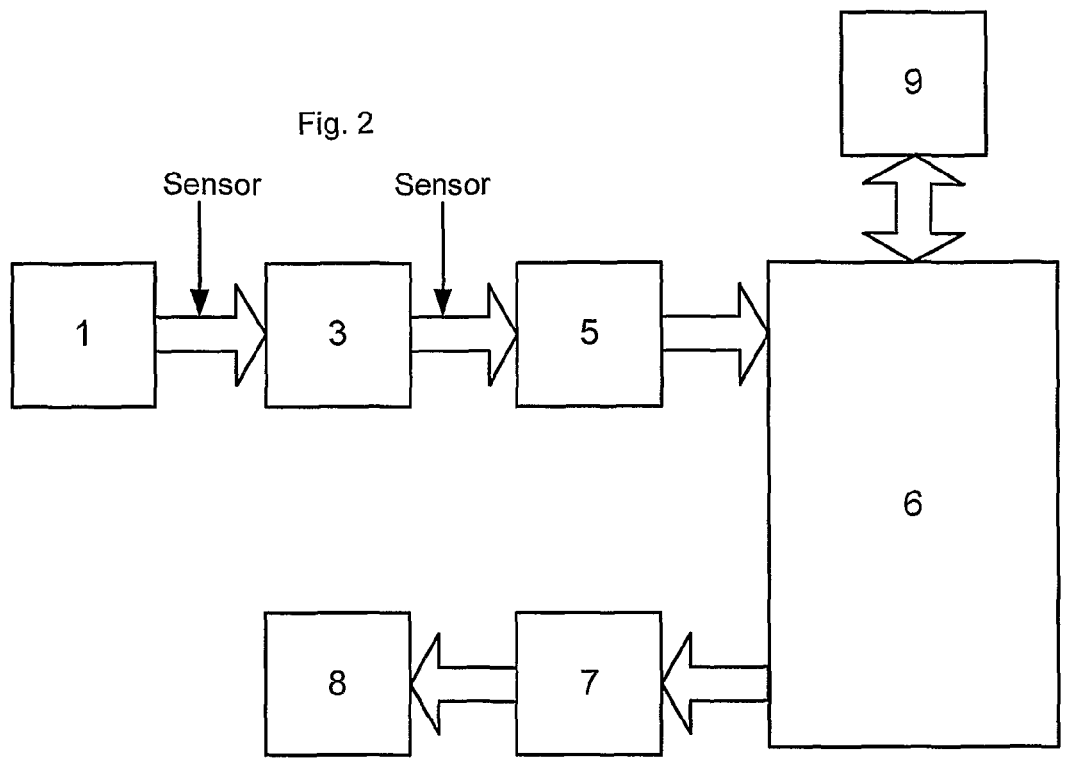

In an alternative embodiment, shown in FIG. 2, one sensor is placed between the fan 1 and the nebuliser 3, and another sensor is placed between the nebuliser 3 and the inlet valve 5 to the sterilisation chamber. The mass gas flow and mass aerosol in the gas flow readings can thus be made simultaneously, unlike the first method which requires the readings to be some time apart.

The sensor preferred in the present invention is one based around the use of an element that consists of an electrical heating component and a temperature sensing component. Preferably, the element is made up of a single component that can perform both functions, such as a RTD or a transistor. However, those in the art will know of other means to achieve said functionality, such as a thermocouple thermally coupled to a resistive heater element, and such apparatus is considered to not depart from the spirit of the invention.

RTD's are well known for in relation to determine temperature, and operate on the principle that the resistance of metals, in particular platinum wire, is sensitive to the temperature at which the resistance is measured. In the case of a platinum wire RTD, a 1° C. change in temperature corresponds to about 0.4Ω change in resistance. Also, platinum wire has the desirable property that the response is relatively linear over a modest temperature range.

RTD's typically have a thin metal film resistance that is silk screened or vacuum sputtered onto a ceramic substrate and an overlying glass passivation layer. These sensors are low in cost, robust, and importantly are unaffected by exposure to potentially destructive sterilants such as hydrogen peroxide.

In use, RTD's indirectly measure temperature by electronically measuring the electrical resistance of the sensor and deriving the temperature from equations generally of the form:—

$$R(t)=R(0)(1+a*T)$$

where $R(0)$ is the resistance at 0° C. and is a constant for the sensor, T is the temperature in ° C. and "a" is also a constant for the sensor.

Resistance is measured by passing a current through the sensor and measuring the voltage drop across it. When used to measure temperature, the RTD measurement current is typically kept small, to about 1 ma or less, to avoid self-heating due to power dissipation in the sensor.

However, in the present case, the RTD is used in a very different fashion to that used for typical temperature measurement.

Figure 3:
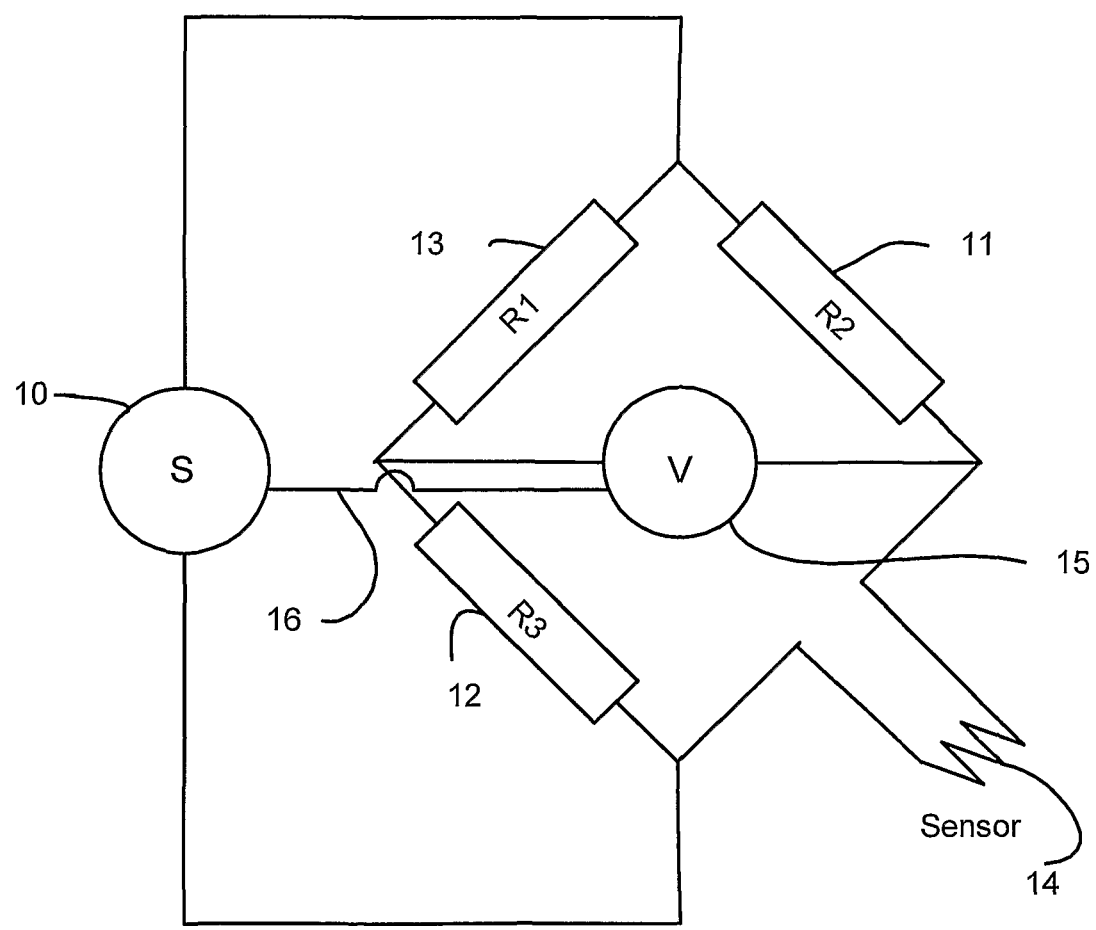

RTD's can operate via a circuit not unlike a Wheatstone bridge, and a simplified circuit layout is shown in FIG. 3. Power source 10 puts out a flow of current into a circuit that can be completed by two competing resistive pathways. One resistive pathway, via R1 and R3 is of known resistance. The other resistive pathway comprises known resistance R2 and a variable resistance in the form of the platinum wire sensor 14. There is a voltage difference across the two pathways which reflects the relative resistance of each. This voltage difference is measured by potentiometer 15 (which is of sufficiently high resistance as to keep the resistive pathways above separate). In the conventional operation of an RTD, the voltage drop allows calculation of the resistance of the sensor 14, the only variable in the system. The resistance of sensor 14 is then correlated with its temperature.

In the present invention, the circuit is operated with sufficient power to heat sensor 14 (which is a platinum wire encased in a glass casing) to a suitable temperature to maintain an appropriate level of aerosol evaporation in a gas flow. The present invention further includes a feedback loop 16 between potentiometer 15 and power source 10, such that when the resistance of the sensor begins to decrease, the power output is increased to maintain a constant resistance. This enables the power source 10 to be operated in a manner such that a constant voltage difference across the balanced circuits is maintained, which consequently results in sensor 14 being maintained at a constant temperature.

The amount of power required to maintain the sensor at a constant temperature, i.e. the amount of power dissipation through the sensor wire reflects the total amount of cooling (gas flow plus evaporation) occurring on the sensor. The greater the cooling effect, the more power required.

Power dissipation in the sensor is employed to achieve a degree of self heating of the sensor so that cooling effects can be measured. Measuring the density of nebulant in an aerosol flow at constant temperature has been found to be free of thermal runaway problems and produces a very fast sensor response, since temperature changes are momentary and small. Accordingly use of an RTD sensor at constant temperature is highly preferred, and the data herein shows that the method described with reference to FIG. 3 produces reliable, reproducible and accurate data.

It should be noted that RTD's could be used in other ways to determine aerosol density in a gas flow, for example, the device could be operated at a constant voltage, however this has been found to be relatively insensitive (compared to constant power) especially at low air speeds.

Alternatively, the RTD may be used at constant current, however this has been found to involve a risk of overheating.

Other variations are also contemplated, for example, the surface temperature of a sensor heated at a constant power could be measured by means of infra red radiation emitted by the surface.

The aerosol sensors of the present invention can be used for the monitoring and control of sterilizers by using the feedback from the sensor in a variety of different ways. For example, if the sensor detects a drop in aerosol density, the relevant control system can increase aerosol flow rate, nebuliser output or both. Flow rate can be modified by changing the fan speed (or the voltage to the fan). Nebuliser output can be modified by controlling the electronic power provided to the nebuliser disc. It is generally preferable to maintain a constant gas flow and use the sensor to control nebuliser output in order to maintain aerosol density to within certain limits. By using the feedback from the sensor in these ways, the flow of a predetermined aerosol concentration past the mist sensor can be maintained for the duration of the aerosol delivery phase. The time of aerosol delivery can also be controlled. By applying a known density of aerosol for a known time, the delivery of a known dosage can be achieved.

When an aerosol flow contacts a surface, there is a cooling effect, due to the microdroplets landing on the surface and evaporating and also due to the gas flow. The external cooling caused by the mist causes greater heat dissipation via the sensor than would be seen under normal atmospheric temperatures—the more the surface is cooled by the mist, the more power needs to be maintained to keep the RTD sensor at any given temperature.

The amount of cooling reflects the amount of liquid in the droplets hitting the surface, and the flow rate of the carrier gas. The component of cooling caused by the flow of the carrier gas can be determined accurately by other means, and thus a baseline for this can be readily established. Baseline values for the cooling effect of the carrier gas can be established for a whole matrix of gases, flow rates, temperatures and humidities. For a known gas (eg air) at known (measured) temperature and humidity, the present apparatus can be used to determine the flow rate.

Once the underlying gas value is subtracted, the cooling effect is directly proportional to the aerosol density.

Further, because the RTD is heated, an operating temperature can be chosen which is such that it allows rapid measurement of the mist density, by speeding the evaporation of condensed mist at such a rate that evaporation exceeds condensation. If the temperature is too low, the mist will soon begin to accumulate on the sensor, causing it to be come drenched in sterilant—as would be seen for any sort of unheated detector in an aerosol flow.

The present invention thus enables both the density of the aerosol in the gas stream and the flow rate of the gas stream to be determined and consequently a dose of aerosol delivered by the gas stream can be precisely determined.

The claims defining the invention are follows:

1. A method of sterilizing, for the purpose of certifying as sterile, an article by contacting said article a sterilant aerosol, and wherein dosage of the sterilant aerosol is measured by:
   1) measuring a density of the sterilant aerosol suspended in a gas stream by:
      i) passing a first gas stream at a flow rate past a first electrically heated element and measuring a first cooling effect;
      ii) passing the sterilant aerosol suspended in a second gas stream at the flow rate for an aerosol delivery time past a second electrically heated element and measuring a second cooling effect;
      iii) measuring a difference between the first cooling effect and second cooling effect and correlating said difference with the density; and
   2) using the flow rate, the aerosol delivery time, aerosol concentration and the density to calculate an amount of aerosol delivered.

2. The method of claim 1, further comprising:
   comparing the amount of aerosol delivered with a predetermined certification dosage; and
   certifying the article as sterile if the amount of aerosol delivered is at or greater than the predetermined certification dosage, or not certifying the article as sterile if the amount of aerosol delivered is less than the predetermined certification dosage.

3. The method of claim 1, further comprising:
   comparing the amount of aerosol delivered with a predetermined certification dosage range; and
   certifying the article as sterile if the amount of aerosol delivered is within the predetermined certification dosage range, or not certifying the article as sterile if the amount of aerosol delivered is not within the predetermined certification dosage range.

4. The method according claim 1, wherein the sterilant aerosol comprises an aerosol of aqueous hydrogen peroxide.

5. The method according to claim 1, wherein at least one of the first or second gas stream comprises air.

6. The method according to claim 1, wherein the flow rate is a known flow rate.

7. The method according to claim 1, wherein a known quantity of aerosol is delivered.

8. The method according to claim 1, wherein a temperature of at least one of the first or second electrically heated element is greater than or equal to a vaporisation point of said sterilant aerosol.

9. The method according to claim 1, wherein at least one of the first or second electrically heated element is coupled to a temperature sensitive element that measures a temperature of said at least one of the first or second electrically heated element.

10. The method according claim 9, wherein at least one of said first or second cooling effect is measured by using said temperature sensitive element in a feedback loop control system to electrically maintain said at least one of the first or second electrically heated element to a preset temperature, wherein at least one of said first or second cooling effect is measured based on a heating effort required or part thereof to maintain said preset temperature.

11. The method according to claim 9, wherein at least one of said first or second cooling effect is measured by using said temperature sensitive element to measure a temperature of said at least one of the first or second electrically heated element, wherein at least one of said first or second cooling effect is measured by measuring the temperature of said at least one or the first or second electrically heated element.

12. The method according to claim 9, wherein at least one of said first or second electrically heated element or said temperature sensitive element is a resistance temperature detector.

13. The method according to claim 12, wherein the resistance temperature detector is flat film type.

14. The method according to claim 9, wherein at least one of said first or second electrically heated element or said temperature sensitive element is a transistor.

15. The method according to claim 9, wherein said at least one of the first or second electrically heated element and said temperature sensitive element are one and the same.

16. The method according to claim 1, wherein the density is measured by a circuit that comprises at least a resistive heater maintained at a steady state temperature.

17. The method according to claim 1, further comprising:
measuring the flow rate of at least one of the first or second gas stream by comparing at least one of the first or second cooling effect on a sensor of gas flow with predetermined values for cooling effect of gas flow rate.

18. The method according to claim 17, wherein the predetermined values for the cooling effect of gas flow rate are determined at given temperatures and humidities.

19. The method according to claim 1, wherein the first and second electrically heated element are one and the same, or are different.

20. A method of maintaining a constant flow of an aerosol comprising:
1) measuring a density of the aerosol suspended in a gas stream by:
i) passing a first gas stream at a flow rate past a first electrically heated element and measuring a first cooling effect;
ii) passing the aerosol suspended in a second gas stream at the flow rate for an aerosol delivery time past a second electrically heated element and measuring a second cooling effect;
iii) measuring a difference between the first cooling effect and second cooling effect and correlating said difference with the density;
2) maintaining the second constant cooling effect at a constant or predetermined value.

21. The method according to claim 20, wherein the first and second electrically heated element are one and the same, or are different.

22. The method according to claim 20, further comprising:
2) maintaining the second constant cooling effect for a predetermined time at a predetermined value, thereby to provide a known dosage of the aerosol.

23. The method according to claim 22, wherein the flow rate is controlled based on a fan speed.

24. The method according to claim 22, wherein the density is controlled based on a nebuliser output.

25. The method according to claim 20, wherein the second cooling effect is maintained at a constant value.

* * * * *